United States Patent [19]

Smith et al.

[11] Patent Number: 5,334,526
[45] Date of Patent: Aug. 2, 1994

[54] **CLONING AND EXPRESSION OF *ALUI* RESTRICTION ENDONUCLEASE**

[75] Inventors: Michael D. Smith; Brian J. Schmidt, both of Rockville; Mary C. Longo, Germantown; Deb K. Chatterjee, N. Potamac, all of Md.

[73] Assignee: Life Technologies, Inc., Gaithersburg, Md.

[21] Appl. No.: 68,188

[22] Filed: May 28, 1993

[51] Int. Cl.$^5$ .................... C12N 9/22; C12N 15/63; C12N 15/70
[52] U.S. Cl. ................ 435/199; 435/252.33; 435/320.1; 435/193
[58] Field of Search .............. 435/199, 193, 252.33, 435/320.1

[56] References Cited

U.S. PATENT DOCUMENTS

| | | | |
|---|---|---|---|
| 4,983,542 | 1/1991 | Van Cott et al. | 435/172.3 |
| 4,996,151 | 2/1991 | Brooks et al. | 435/172.3 |
| 5,002,882 | 3/1991 | Lunnen et al. | 435/172.3 |
| 5,082,784 | 1/1992 | Chatterjee et al. | 435/252.3 |
| 5,147,800 | 9/1992 | Hammond et al. | 435/252.3 |
| 5,179,015 | 1/1993 | Wilson et al. | 435/172.3 |
| 5,200,333 | 4/1993 | Wilson | 435/172.3 |

FOREIGN PATENT DOCUMENTS

| | | |
|---|---|---|
| 0193413 | 9/1986 | European Pat. Off. |
| WO91/14771 | 10/1991 | PCT Int'l Appl. |

OTHER PUBLICATIONS

Brooks et al., Cloning the *Bam*HI restriction modification system, *Nucleic Acids Research* 17(3):979-997 (1989).

Darzins et al., Cloning of Genes Controlling Alginate Biosynthesis from a Mucoid Cystic Fibrosis Isolate of *Pseudomonas aeruginosa*, *Journal of Bacteriology* 159(1):9-18 (Jul. 1984).

Hammond et al., Cloning the *Kpn*I restriction-modification system in *Escherichia coli*, *Gene* 97:97-102 (1991).

Howard et al., Cloning the *Dde*I restriction-modification system using a two-step method, *Nucleic Acids Research* 14(20):7939-7951 (1986).

Janulaitis et al., Cloning of the modification methylase gene of *Bacillus centroporus* in *Escherichia coli*, *Gene* 20:197-204 (1982).

Kiss et al., Molecular cloning and expression in *Escherichia coli* of two modification methylase genes of *Bacillus subtilis*, *Gene* 21:111-119 (1983).

Lunnen et al., Cloning type-II restriction and modification genes, *Gene* 74:25-32 (1988).

Mann et al., Cloning of Restriction and Modification Genes in *E. coli*: The *Hha*II System From *Haemophilus haemolyticus*, *Gene* 3:97-112 (1978).

Piekarowicz et al., A new method for the rapid identification of genes encoding restriction and modification enzymes, *Nucleic Acids Research* 19(8):1831-1835 (1991).

Roberts, R. J., Restriction enzymes and their isoschizomers, *Nucleic Acids Research* 17(Suppl):r347-r387 (1989).

Stratagene Catalog p. 92 (1989).

Szomolanyi et al., Cloning the modification methylase gene of *Bacillus sphaericus* R in *Escherichia coli*, *Gene* 10:219-225 (1980).

Walder et al., Cloning of the *Msp*I Modification Enzyme, The Site of Modification and Its Effects on Cleavage by *Msp*I and *Hpa*II, *The Journal of Biological Chemistry* 258(2):1235-1241 (Jan. 25, 1983).

Wilson, G. G., Cloned restriction-modification systems—a review, *Gene* 74:281-289 (1988).

Wilson, G. G., Organization of restriction-modification systems, *Nucleic Acids Research* 19(10):2539-2566 (1991).

Wilson, G. G., Type II restriction-modification systems, *TIG* 4(11):314-318 (Nov. 1988).

*Primary Examiner*—Charles L. Patterson, Jr.
*Attorney, Agent, or Firm*—Sterne, Kessler, Goldstein & Fox

[57] ABSTRACT

The present invention is directed to recombinant hosts which contain and express the AluI Type-II restriction endonuclease gene. The present invention is also directed to vectors or DNA molecules which contain the gene, and to methods of producing the AluI enzyme. One source of the enzyme is *Arthrobacter luteus*, although other microorganisms may be used to isolate restriction endonuclease isoschizomers of the invention.

22 Claims, No Drawings

CLONING AND EXPRESSION OF ALUI RESTRICTION ENDONUCLEASE

FIELD OF THE INVENTION

The present invention is in the field of genetic engineering and molecular biology. This invention is directed to recombinant hosts expressing restriction endonucleases from the genus Arthrobacter. This invention is specifically directed to the recombinant hosts and vectors which contain the gene coding for the restriction endonuclease AluI. This invention is also directed to the cloned restriction endonuclease isoschizomers of the enzyme.

BACKGROUND OF THE INVENTION

Restriction endonucleases are a class of enzymes that occur naturally in prokaryotic and eukaryotic organisms. When restriction endonucleases are purified away from other contaminating cellular components, the enzymes can be used in the laboratory to cleave DNA molecules in a specific and predictable manner. Thus, restriction endonucleases have proved to be indispensable tools in modern genetic research.

Restriction endonucleases cleave DNA by recognizing and binding to particular sequences of nucleotides (the "recognition sequence") along the DNA molecule. The enzymes cleave both strands of the DNA molecule within, or to one side of, this recognition sequence.

Different restriction endonucleases have affinity for different recognition sequences. About 100 kinds of different endonucleases have so far been isolated from many microorganisms, each being identified by the specific base sequence it recognizes and by the cleavage pattern it exhibits. In addition, a number of restriction endonucleases, called restriction endonuclease isoschizomers, have been isolated from different microorganisms which in fact recognize the same recognition sequence as those restriction endonucleases that have previously been identified. These isoschizomers, however, may or may not cleave the same phosphodiester bond as the previously identified endonuclease.

Modification methylases are complementary to their corresponding restriction endonucleases in that they recognize and bind to the same recognition sequence. However, in contrast to restriction endonucleases, the modification methylases chemically modify certain nucleotides within the recognition sequence by the addition of a methyl group. Following this methylation, the recognition sequence is no longer bound or cleaved by the restriction endonuclease. Thus, in nature, methylases serve a protective function, i.e., to protect the DNA of an organism which produces its corresponding restriction enzyme.

Restriction enzymes and modification methylases can be purified from the host organism by growing large amounts of cells, lysing the cell walls, and purifying the specific enzyme away from the other host proteins by extensive column chromatography. However, the amount of restriction enzyme relative to that of the other host proteins is usually quite small. Thus, the purification of large quantities of restriction enzymes or methylases by this method is labor intensive, inefficient, and uneconomical.

An alternative method for producing large quantities of restriction and modification enzymes is to clone the genes encoding the desired enzymes and overexpress the enzymes in a well studied organism, such as *Escherichia coli(E. coli)*. In this way, the amount of restriction and modification enzymes, relative to that of the host proteins, may be increased substantially. The first cloning of a DNA endonuclease gene was described by Mann et al. *Gene* 3:97–112 (1978). Since then more than seventy DNA methylase and restriction endonucleases have been cloned. Thus far, the majority of the restriction endonuclease genes are closely linked to their corresponding methylase genes.

Restriction-modification systems can be cloned by several methods. A number of endonuclease and methylase genes have been cloned from endogenous plasmids: EcoRII (Kosykh et al., *Mol. Gen. Genet.* 178:717–718 (1980)), EcoRI (Newman et al., *J. Biol. Chem.* 256:2131–2139 (1981)), Greene et al., *J. Biol. Chem.* 256:2143–2153 (1981)), EcoRV (Bougueleret et al., *Nucl. Acids Res.* 12:3659–3676 (1984)), PvuII (Blumenthal et al., *J. Bacteriol.* 164:501–509 (1985)), and PaeR71 (Gingeras et al., *Proc. Natl. Acad. Sci. USA* 80:402–406 (1983)). An alternative method of cloning is the phage restriction method in which bacterial cells carrying cloned restriction and modification genes survive phage infection (Mann et al., supra; Walder et al., *Proc. Natl. Acad. Sci. U.S.A.* 78:1503–1507 (1981); Rodicio et at., *Mol. Gen. Genet.* 213:346–353 (1988)). Another procedure is based upon methylation protection and has been suggested by Mann et at., supra, and Szomolanyi et al., *Gene* 10:219–225 (1980). This latter scheme involves digestion of a plasmid library with the restriction enzyme to be cloned. Only those plasmids with DNA sequences modified by the corresponding methylase will be resistant to digestion and will produce transformants in a suitable host. This selection method has been used to clone endonuclease and methylase genes together as well as to clone methylase genes alone (Szomolanyi et at., supra; Janulaitis et al., *Gene* 20:197–204 (1982); Walder et al., *J. Biol. Chem.* 258:1235–1241 (1983); Kiss et al., *Gene* 21:111–119 (1983); Wilson, *Gene* 74:281–289 (1988)). However, this technique sometimes yields only the methylase gene, even though the endonuclease and modifying genes are closely linked.

A multi-step approach has been required to clone certain restriction-modification systems in *E. coli*, including DdeI (Howard et al., *Nucl. Acids Res.* 14:7939–7950 (1989)), BamHI (Brooks et al., *Nucl. Acids Res.* 17:979–997 (1989)), and KpnI (Hammond et al., supra). In each case, protection of the host with methylase expressed on a plasmid was necessary to stabilize a compatible vector containing the functional endonuclease gene. Wilson, supra, has proposed a model to explain why certain restriction-modification systems must be cloned utilizing a protected host. This model proposes that in order to establish a plasmid carrying a restriction-modification system, methylase protection must occur at a rate that is greater than the rate of endonuclease digestion. Otherwise, restriction enzymes would cleave unmethylated plasmid and/or genomic DNA and degrade the plasmid and/or kill the host. Although this model is a plausible explanation of plasmid establishment, it has yet to be determined whether continued independent expression of methylase from a separate plasmid is necessary to maintain the plasmid carrying the restriction-modification system during cell growth and replication.

SUMMARY OF THE INVENTION

The present invention is directed to recombinant hosts which contain and express the Type-II restriction endonuclease gene of the present invention. The restriction endonuclease of the invention recognizes the palindromic sequence:

5' AGCT 3'
3' TCGA 5'.

The isoschizomers of this class of restriction endonucleases are exemplified by AluI and cleave the sequence between the deoxyguanidine (G) and deoxycytidine (C) residues:

5' AG ↓ CT 3'
3' TC ↑ GA 5'.

This invention is further directed to vectors comprising an Arthrobacter gene coding for the restriction endonuclease.

This invention is further directed to processes for obtaining the enzyme and the use thereof. According to the process of this invention, the restriction endonuclease is produced by culturing a recombinant host comprising an Arthrobacter gene for the restriction endonuclease and modification methylase, and isolating enzymes from the recombinant host.

In particular, the present invention is concerned with genes coding for restriction endonuclease, AluI.

Definitions

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified enzyme is essentially free from contaminating cellular components, said components being associated with the desired enzyme in nature, as evidenced by a single band following polyacrylamide-sodium dodecyl sulfate gel electrophoresis. Contaminating cellular components may include, but are not limited to, phosphatases, exonucleases or other undesirable endonucleases.

Restriction endonuclease isoschizomer. A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer. A modification methylase isoschizomer is a term used to designate a group of modification methylases that recognize the same recognition sequence but are isolated from different microbial sources. Modification methylase isoschizomers may or may not chemically modify the same nucleotides within the recognition sequence as the restriction endonuclease with which it is being compared.

Recognition sequence. Recognition sequences are particular DNA sequences which a restriction endonuclease or a modification methylase recognizes and binds. Recognition sequences are typically four to six (and in some cases, eight) nucleotides in length with a two-fold axis of symmetry.

Recombinant Host. According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism. The term "recombinant host" is not meant to include the wild type Arthrobacter strain which produces AluI.

Recombinant vector. Any cloning vector or expression vector which contains the desired cloned gene(s).

Host. Any prokaryotic or eukaryotic microorganism that is the recipient of a replicable expression vector or cloning vector. A "host," as the term is used herein, also includes prokaryotic or eukaryotic microorganisms that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Nomenclature for naming restriction endonucleases are in accord with the proposal of Smith et al., *J. Mol. Biol.* 81:419–423 (1973). Briefly, the first letter "A" of AluI designates the genus "Arthrobacter" while the lower case letters "lu" designate the species "luteus." Thus, the original strain found to produce AluI was designated Arthrobacter luteus.

DETAILED DESCRIPTION OF THE INVENTION

This invention is directed to recombinant hosts which express the gene coding for the Type-II restriction endonuclease AluI and to DNA molecules which contain the gene. AluI recognizes the palindromic sequence 5' AGCT3', cleaving between the G and C residues, producing blunt-ended DNA molecules. The double-stranded recognition site of AluI is thus characterized as follows:

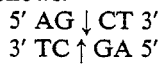

(wherein A represents deoxyadenine, T represents deoxythymidine, G represents deoxyguanidine, and C represents deoxycytidine).

This present invention is further directed to recombinant hosts and DNA molecules which contain genes coding for isoschizomers of the restriction endonuclease of the present invention. Methods for producing the enzymes of the invention are also disclosed.

I. Isolation of the Genes Coding for the Restriction Endonuclease and Modification Methylase or Isoschizomers Thereof The restriction endonuclease (AluI) and its corresponding modification methylase may be obtained from any strain of *A. luteus*. Genes coding for isoschizomers of these enzymes can be obtained from any genus including, but not limited to, Arthrobacter, Bacillus, Citrobacter, Enterobacter, Escherichia, Flavobacterium, Caryophanon, Klebsiella, Micrococcus, Xanthomonas, Nocardia, Pseudomonas, Salmonella, and Streptomyces. The preferred genus to isolate isoschizomers of the restriction endonuclease of the present invention is Arthrobacter. The preferred species for obtaining the gene encoding the enzyme of the present invention is *Arthrobacter luteus* as described in the examples.

Cloning and Expressing the Genes Coding for the Restriction Endonuclease and Modification Methylase or Isoschizomers Thereof AluI and AluI methylase are preferably obtained by isolating the genes coding for the enzymes from *Arthrobacter luteus* and then cloning and expressing them. It is understood in this invention that genes coding for isoschizomers of the restriction endonucleases and modification methylases of the present invention may be obtained from any microorganism including the genus Arthrobacter by using the recombinant techniques described herein.

DNA molecules which code for AluI and AluI methylase, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including restriction digestion to provide appropriate termini, filling in of cohesive ends as appropriate, alkaline phosphatase treatment to avoid undesirable joining, and ligation with appropriate ligases.

a. Hosts for Cloning and Expressing

The present invention encompasses the expression of the desired restriction endonuclease in prokaryotic and eukaryotic cells. Eukaryotic and prokaryotic hosts that may be used for cloning and expressing the enzymes of the invention are well known in the art. Vectors which replicate in such host cells are also well known (Maniatis et al., *Molecular Cloning: A Laboratory Manual*, Cold Spring Harbor Laboratory Press, Cold Spring Harbor, N.Y. (1982)).

Preferred prokaryotic hosts include, but are not limited to, bacteria of the genus Escherichia, Bacillus, Streptomyces, Arthrobacter, Pseudomonas, Salmonella, Serratia, Caryophanon, etc. The most preferred prokaryotic host is *E. coli*. Bacterial hosts of particular interest in the present invention include *E. coli* DH10B::rec+.

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either on cytosine residues or adenine residues. Specifically, the well known methylcytosine-specific systems include mcrA (rglA), and mcrB (rglB) (Revel et al., *Virology* 31:688–701 (1967); Raleigh et al., *Proc. Natl. Acad. Sci. USA* 83:9070–9074 (1986)). The methyladenine-specific restriction system has been designated mrr (Heitman et al., *J. Bacteriol.* 169:3243–3250 (1987)). Thus, the preferred host for cloning and expressing the genes encoding for the enzymes of the present invention are hosts in which these types of restriction systems have been inactivated through mutation or loss.

b. Methods for Cloning and Expressing

AluI and AluI methylase, or isoschizomers thereof, are preferably obtained by isolating the genes coding for the enzymes and then cloning and expressing them. Four different techniques for isolating and cloning restriction endonucleases and modification methylases have been described in a review by Wilson, *Gene* 74:281–289 (1988). The four methods reviewed include: (1) subcloning of natural plasmids; (2) selection based on phage restriction; (3) selection based on vector modification involving methylation protection; and (4) multi-step isolation.

The methylation protection method for cloning restriction endonuclease genes relies on the proximity of the methylase and restriction enzyme genes to each other and on the expression of both genes in the host cell such as *E. coli*. First, a library is constructed by ligating fragmented genomic DNA from the source organism into a vector. For this library, one chooses a vector having one or, preferably, more recognition sites of the restriction enzyme one wishes to clone. Preferably, vector pCP13 is used to construct the plasmid library (Darzins, A. et al., *J. Bacteriol.* 159:9–18 (1984)). Generally, library inserts are prepared by only partially digesting the genomic DNA in order to obtain a portion of DNA fragments which contain the intact gene of interest. Second, this library is introduced into and grown in a suitable host such as *E. coli* and subsequently, isolated from these grown cells. The library is called the plasmid library. The plasmid library is a mixture of different DNA molecules, having virtually all possible inserts and thus, is representative of most, if not all, DNA sequences contained in the source organism. The vector/insert combinations having a methylase gene will have methylated the recognition sequences within the vector/insert DNA and the host chromosomal DNA if the methylase is expressed in the host used, preferably, *E. coli*.

The isolated plasmid library DNA is then digested with the restriction enzyme. Unmethylated vector/insert combinations are degraded and methylated combinations survive the endonuclease treatment. The endonuclease-treated DNA is then introduced into a fresh host cell. Digested vector/insert combinations do not become established in the host cell. Methyl-protected vector/insert combinations, which survived the endonuclease treatment, can establish and maintain themselves in the new E. coli host cells, thereby forming clones.

Cell extracts of these clones are then assayed for restriction endonuclease activity in order to identify clones which express the desired restriction enzyme. Thus, genes for a methylase-restriction system can be cloned on a single recombinant DNA molecule, provided that the restriction endonuclease gene is contained on that fragment.

There are a number of reasons why the above method might not work with a particular endonuclease-methylase system. (1) The two genes (methylase and endonuclease) may not be closely linked. In that case, both genes cannot be on the same DNA fragment insert. (2) The cloned fragment may, by chance, contain only the methylase gene. For example, a closely linked endonuclease gene might be inactivated by being cut by the restriction enzyme that generated the DNA library. Similarly, the methylase and endonuclease genes may have been separated from each other by a cleavage at an intervening restriction site. (3) The level of expression of the endonuclease may be high relative to the expression level of the methylase. In this situation, before the expressed methylase can protect the host DNA, the expressed endonuclease destroys the vector/insert combination as well as the chromosome and may kill the host cell. Alternatively, a rearrangement(s) (i.e., an insertion(s) or deletion(s)) resulting in loss of part or all of the endonuclease gene from the vector/insert combination may allow the host to survive. (4)The methylase gene may not be expressed in the new host, leading to lack of protection of DNA from the endonuclease. (5) The endonuclease gene may not be expressed in the new host. In situations (1) and (3), if the endonuclease is expressed in the host, there will be no methylase enzyme activity to protect DNA in the host cell and the attempt to clone the endonuclease would fail.

Surprisingly, the usual methods for cloning a restriction-modification system by methylation protection were unsuccessful for the AluI restriction/modification system. Results from the hybridization analyses indicated that the sequences of the DNA near the AluI restriction enzyme coding genes isolated from AluI methylase positive clones differed from the sequences adjacent to AluI methylase genes in the *A. luteus* chromosome. In contrast, the DNA library, which has not been selected with AluI/PvuII restriction enzyme, showed no rearrangement near the AluI genes. Therefore, the rearrangement(s) occurred after the selection.

One hypothesis that could explain this unexpected result was that the AluI restriction enzyme coding gene was closely linked to the AluI methylase gene in the *A. luteus* chromosome but that methylase gene expression was too low to protect all of the AluI sites in the host chromosome. In this case, the only clones surviving would be those in which the link between AluI restriction endonuclease and AluI methylase was disrupted by a rearrangement of the DNA. In vitro digestion of the clones containing the AluI genes cleaved all the unmethylated sites, and following transformation, the plasmid circularized by gene rearrangements. This situation is unexpected and unique because in other cases such as BamHI (see U.S. Pat. No. 5,137,823) or KpnI (see U.S. Pat. No. 5,082,784) the rearrangement occurred in the library itself, i.e. before methylase selection. These observations may explain the failure of others to clone the AluI endonuclease (for example, see Lunnen et al., *Gene* 74:25–32 (1988)).

In the present invention, genomic DNA was isolated from an AluI producing strain of *Arthrobacter luteus*. Using standard techniques well-known to those in the art, a recombinant DNA library was constructed, the library was introduced into a bacterial host, and DNA insert/vector molecules were isolated from host cells.

A portion of the first DNA library was digested with AluI or PvuII and the resulting DNA digest was introduced into new E. coli DH10B (rec[31]) host cells. PvuII recognizes tile sequence: 5' CAGCTG3', and the internal four-base sequence (i.e., AGCT) is the AluI sequence. Clones were selected and DNA samples from these clones were screened for resistance to digestion with AluI or PvuII. Clones containing DNA resistant to AluI or PvuII harbored insert/vector combinations that carried tile AluI methylase. Although tile transformants express AluI methylase activity, AluI endonuclease activity was not detectable.

In order to clone tile AluI endonuclease, a second genomic library was constructed in a rec+ host strain. Although tile first genomic library was constructed in a rec− E. coli host, a rec+ strain was chosen as the host for the second genomic library because the RecA protein is required for homologous genetic recombination and DNA repair (Radding, C. M., *Ann. Rev. Biochem.* 47:847–880 (1978)). Therefore, a rec+ host strain should be able to repair DNA which is cleaved by AluI due to inadequate protection by AluI methylase. Typically, rec+ host strains not are used in cloning procedures because tile RecA protein catalyzes homologous recombination ill cloned DNA (*Current Protocols in Molecular Biology*, Ausubel et al. (Eds.), John Wiley & Sons, pp.1.4.6–1.4.7 (1987)).

A DNA probe containing AluI methylase DNA sequences was used to identify colonies of transformants which contained the AluI methylase gene. The DNA from colonies producing a signal were purified and analyzed by digestion with AluI. The clones with DNA that were resistant to AluI digestion were then tested for AluI endonuclease activity.

Although the steps outlined above are the preferred mode for practicing the present invention, it will be apparent to those skilled in the art that the above-described approach can vary in accordance with techniques known in the art. For example, once the AluI methylase and/or restriction genes are cloned based on the information disclosed herein, these gene sequences or synthetic oligonucleotides of these sequences may be used in hybridization experiments with genetic material from different organisms to obtain clones which contain these genes. See Maniatis et al., supra. Furthermore, one of ordinary skill in the art, using standard hybridization techniques, can utilize these sequences to isolate genes which code for isoschizomers of the AluI restriction and modification enzymes by altering the hybridization stringencies.

Methods for Enhancing Expression

Once the desired restriction endonuclease gene has been isolated, a number of recombinant DNA strategies exist for enhanced production of the desired protein in eukaryotic or prokaryotic hosts. These strategies, which will be appreciated by those skilled in the art, utilize high copy number cloning vectors, expression vectors, inducible high copy number vectors, etc.

Enhanced production of the restriction endonuclease can be accomplished, for example, by operably linking the desired gene to a strong prokaryotic promoter, although the natural restriction gene promoter may be used. Such well known promoters may be either constitutive or inducible. Examples of constitutive promoters include the int promoter of bacteriophage λ, and the bla or tet promoter of the β-lactamase gene or tetracycline resistance gene of pBR322, respectively. Examples of inducible prokaryotic promoters include the major left and right promoters of bacteriophage λ ($P_L$ and $P_R$), the trp, recA, lacZ, gal, trc, and tac promoters of E. coli, the α-amylase (Ulmanen, I., et al., J. Bacteriol. 162:176–182 (1985)), the $\delta^{28}$-specific promoters of B. subtilis (Gilman, M. Z., et al., Gene 32:11–20 (1984)), the promoters of the bacteriophages of Bacillus (Gryczan, T. J., In: The Molecular Biology of the Bacilli, Academic Press, Inc., N.Y. (1982)), and Streptomyces promoters (Ward, J. M., et at., Mol. Gen. Genet. 203:468–478 (1986)). Prokaryotic promoters are reviewed by Glick, B. R., (J. Ind. Microbiol. 1:277–282 ( 1987)); Cenatiempo, Y. (Biochimie 68:505–516 (1986) ); and Gottesman, S. (Ann. Rev. Genet. 18:415–442 (1984)).

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Furthermore, those skilled in the art will recognize that various combinations of maintaining both the modification and restriction genes within the same recombinant host can be constructed. The only requirement, when cloning restriction endonuclease genes, is that the recombinant host contain and express the methylase gene corresponding to the endonuclease gene being cloned.

III. Isolation and Purification of the Restriction Endonuclease from Recombinant Hosts The enzyme of this invention, AluI, or isoschizomers thereof, is preferably produced by fermentation of the recombinant host (prokaryotic or eukaryotic) containing and expressing the cloned restriction endonuclease gene. The recombinant host, such as E. coli, producing the cloned protein, can be grown and harvested according to techniques well known in the art.

After culturing, the recombinant host cells of this invention can be separated from the culture liquid, for example, by centrifugation. The restriction enzymes produced by this host can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, desired enzyme can be purified by extraction, ion-exchange chromatography, molecular-sieve chromatography, affinity chromatography, and the like, giving the restriction endonuclease of this invention.

According to the present invention, assays to detect the presence of the restriction endonucleases and modification methylases can be used during the conventional biochemical purification methods to determine the presence of these enzymes.

The restriction endonuclease can be identified on the basis of the cleavage of its recognition sequence. For example, lambda (λ) DNA can be used as a substrate. After digestion with endonuclease, the DNA fragments are separated electrophoretically in agarose gels in the buffer systems conventional for fragment separation and in the presence of ethidium bromide (EtdBr).

Demonstration of modification methylase activity can be, but is not limited to, a two-step identification process. First, substrate DNA (λDNA) that contains the recognition sequence is incubated with column fractions to be tested for methylase activity. Second, this DNA is then challenged with the corresponding restriction activity to identify those fractions which contain methylase activity. For example, while assaying for AluI methylase, the DNA samples will be challenged with AluI. Thus, DNA samples which do not exhibit cleavage with AluI contain AluI methylase activity.

The recombinant host (E. coli DH10B::recA+) containing the genes encoding for AluI and AluI methylase was put oil deposit with the Patent Culture Collection, Northern Regional Research Center, USDA, 1815 N. University Street, Peoria, Ill. 61604 USA (NRRL) as deposit No. NRRL B-21108.

Having now generally described the invention, the same will be more readily understood through reference to the following Examples which are provided by way of illustration, and are not intended to be limiting of the present invention, unless specified.

EXAMPLE 1

Bacterial Strains and Growth Conditions

E. coli strains were grown at 37° C. in Circle Grow (BIO 101, P.O. Box 2284, La Jolla, Calif., 92038-2284), or in YET broth (5 gm/l yeast extract, 10 gm/l tryptone, and 5 gm/l NaCl) with antibiotic supplements of 100 μg/ml ampicillin (Ap); 15 μg/ml tetracycline (Tc); or 50 μg/ml chloramphenicol, as appropriate. E. coli DH10B competent cells were obtained commercially from Life Technologies, Inc. (LTI; 8717 Grovemont Circle, Gaithersberg, Md. 20884-9980).

Arthrobacter luteus, ATCC 21606, was obtained from the American Type Culture Collection, Rockville, Md.

EXAMPLE 2

DNA Isolation

Small scale plasmid DNA isolations were performed by an alkaline lysis method (Maniatis et at., Molecular Cloning: A Laboratory Manual, Cold Spring Harbor Laboratory, Cold Spring Harbor, N.Y. (1982)). For large scale preparations, alkaline lysis was followed by a standard CsCl (cesium chloride)-ethidium bromide (EtdBr) gradient centrifugation (Maniatis et al., supra).

A. luteus total genomic DNA was isolated according to the procedure described by Marmur, J., J. Mol. Biol. 3:208–218 (1961).

EXAMPLE 3

Construction of Genomic Libraries

Genomic DNA of Arthrobacter luteus (ATCC 21606) was digested partially with HpaII and Sau3AI as follows. Purified genomic DNA (100 μg) was digested in separate reactions with 5, 2.5, 1.25, 0.625, 0.31, 0.156, 0.078, 0.039 u/μl of HpaII in 100 μl of 1X REact 8, or Sau3AI in 100 μl of 1X REact 4. After the samples were incubated 1 hour at 37° C., the DNA was analyzed by agarose gel electrophoresis. An enzyme concentration of 0.039 u/μl provided the conditions necessary for minimal digestion of the genomic DNA in which 90% of the DNA fragments were 15 kilobases (kb) or greater.

The pCP13 vector (3 μg) was digested with ClaI, and ligated with 10 μg of the HpaII-partially digested genomic DNA using one unit of T4 DNA ligase in 1X ligase buffer (LTI). Similarly, 3 μg of BamHI-digested pCP13 vector was ligated with 10 μg of the Sau3AI-partially digested genomic DNA, as described above. Both 30 μl ligation reactions were incubated at room temperature (25° C.) for 16 hours.

Approximately 2 to 2.5 μg of ligated DNA (5 μl of the ligation reaction mixture) from each ligation reaction were packaged using LTI's recommended procedure. After the packaging reaction was complete, E. coli cells were infected with the packaging mix as follows. DH10B cells were prepared by growing an overnight culture in YET media containing 0.2% maltose with 10 mM MgSO$_4$. The next day, 500 μl of these cells were inoculated into 10 ml of YET containing 0.2% maltose with 10 mM MgSO$_4$, and the cells were grown to mid-log phase. The cells were then centrifuged and resuspended in 2.0 ml of sterile 10 mM MgSO$_4$ buffer. One hundred microliters of the cell suspension were mixed with 200 μl of packaging mix. After a 15 minute incubation at 37° C. (without shaking), a 1 volume of SOC medium (2% Bacto tryptone, 0.5% Yeast extract, 10 mM NaCl, 2.5 mM KCl, 10 mM MgCl$_2$, and 20 mM glucose) was added. The cells were allowed to grow at 30° C. in an air shaker-incubator for 60 minutes. The cells were plated onto YET agar plated containing tetracycline, and incubated overnight at 30° C.

The Sau3AI-derived library was unsuccessful. However, approximately 5000 tetracycline resistant colonies were obtained from the HpaII-derived library. The colonies were pooled together by scraping the cells from the agar surface. This was accomplished by flooding each plate with LB medium (10 gm/l bacto-tryptone, 5 gm/l bacto-yeast extract, and 10 gm/l NaCl) to a filial volume of 20 ml. After carefully resuspending the cells with a sterilized glass rod, 18 ml of the cell suspension were immediately inoculated in 500 ml of Circle-Grow media containing tetracycline.

After 4.5 hours of growth at 30° C., the cells were harvested. Plasmid DNA was isolated from this cell suspension according to Example 2. The isolated cosmid library was designated pCPAluL.

EXAMPLE 4

Selection of Clones Expressing Methylase and Restriction Enzymes

Clones expressing the AluI methylase were selected by digesting the cosmid library DNA with an excess amount of AluI and PvuII. To select AluI methylase clones, pCPAluL plasmid DNA (5 μg) was digested in a reaction volume of 50 μl containing 1×REact 1 buffer (LTI) with 50 units of AluI at 37° C. for 2 hours. For PvuII digestions, 50 units of PvuII in 1×React 6 was used. The DNA was dephosphorylated with 5 units of calf intestinal phosphatase at 50° C. for 60 minutes. The DNA was then extracted with an equal volume of phenol:chloroform (1:1), precipitated with ethanol, and dissolved in 10 μl of TE buffer.

E. coliDH10B competent cells were transformed with the digested DNA library according to the manufacturer's suggested protocol. Briefly, 20 μl of cold competent cells were mixed with 1 μl of the AluI or PvuII digested DNA. The cells were incubated without shaking for 30 minutes on ice. After a 45 second heat shock at 42° C., the cells were diluted with 980 μl of SOC, grown for 60 minutes at 30° C, and then plated on YET agar plates containing tetracycline. The AluI- and PvuII-enriched libraries produced 38 and more than 2000 tetracycline resistant colonies, respectively.

Colonies that survived the methylase selection scheme were analyzed for the presence of methylase activity. Twenty-four clones surviving both AluI and PvuII selection were individually inoculated and grown overnight in 3 ml of Circle-Grow medium containing tetracycline. Small scale plasmid isolations were performed as previously described.

The DNA preparations were tested for their ability to resist cleavage with AluI or PvuII as follows. Isolated DNA (0.5 to 1.0 μg) was digested in 1×REact 1 with 10 units of AluI, or in 1×REact 6 with 10 units of PvuII, for 30 minutes at 37° C. Protection of the resident plasmid and the host chromosomal DNA from digestion indicated the presence of methylase activity. Analysis of the plasmid DNA by agarose gel electrophoresis demonstrated that all 24 of the AluI-enriched clones were cleaved by AluI, while 2 of 24 PvuII-enriched clones were not cleaved with PvuII. The two PvuII-enriched clones were identical. One of the two PvuII selected clones (designated as #40) was digested with AluI and demonstrated resistance to digestion. While PvuII demonstrated complete protection, AluI digestion showed only partial protection. Thus, selection with PvuII seems to be essential to obtain an AluI methylase-containing clone.

Although the two PvuII-enriched clones apparently expressed methylase, due to the resistance of plasmid DNA to AluI digestion, neither clone displayed any AluI activity. Thus, an additional selection step was needed to determine whether the AluI gene was active at a low level. Specifically, DNA from clone #40 was partially digested with Sau3AI and ligated with pACYC184 (Chang, A. C. Y. et at., J. Bacteriol. 134:1141–1156 (1978)) which had been digested with BamHI. DH10B cells were transformed, and the plasmid DNA from 12 clones were analyzed by restriction digests. One of the 12 clones demonstrated resistance to AluI and PvuII digestion and was designated pACYCAluMI. The insert size of this clone was 3,600 bp and did not demonstrate AluI restriction activity. Similar subcloning experiments into the high-copy number vectors pTTQ18 (Stark, M. J., Gene 51:255–267 (1987)), pBlueScript (Stratagene Cloning Systems, 11099 North Torrey Pines Road, La Jolla, Calif. 92037), and pUC19 (LTI) also displayed no AluI restriction enzyme activity.

A Southern Blot analysis was performed to determine whether the clones did not express AluI activity because the cloned DNA had been rearranged. The DNA from the A. luteus chromosome, pCPAluL (Example 3), and clone #40 were digested with restriction enzymes, and blotted onto a nylon support membrane filter.

A DNA probe was prepared as follows. pACYCAluMI DNA was digested with 20 units of BamHI and 20 units of BglI in 1 X REact 3. The DNA digest was fractionated using agarose gel electrophoresis (1% agarose gel; run at 180 volts). A 1,400 bp fragment, containing a large portion of the AluI methylase gene, was extracted from the gel, and the DNA was purified from the agarose using Geneclean (BIO 101, La Jolla, Calif.). Approximately 5 ng of the DNA fragment were labelled with biotin using the Photogene Labelling System, and one half of the probe was used to hybridize with the filter as described by the manufacturer (LTI).

The results indicated that the initial library DNA (pCPAluL) did not suffer any rearrangements as determined by the similarity in the banding pattern between the DNA library and the *A. luteus* chromosome. However, the DNA of clone #40, did not share a complementary banding pattern with the chromosome. Therefore, a rearrangement in the DNA of clone #40 must have occurred after the methylase selection. It is possible that the DNA became rearranged because the library DNA was not fully methylated when the library DNA had been digested with PvuII, to select for clones containing the methylase. This situation is quite different from other cases such as BamHI and KpnI, where the rearrangement occurred in the primary or initial library, i.e. before the methylase selection.

The only way to rescue cosmid clones containing contiguous AluI DNA was to use the AluI methylase gene as a probe for screening the initial AluI library DNA by colony hybridization. To further protect the DNA from any possible nicking, a rec+ host strain was used to help repair damaged DNA from any low level expression of the restriction enzyme. This was accomplished by introducing pCPAluL DNA into the competent host strain, DH10B::rec+, and selecting for tetracycline resistance.

Approximately 2,000 colonies were transferred to a nylon support membrane and processed for colony hybridization. Briefly, the filters were treated at room-temperature (23° C.) for 3 minutes with 10% SDS (sodium dodecyl sulfate) followed by treatment with 0.5M NaOH, 1.0M NaCl for 5 minutes; then 0.5M Tris-HCl (pH 8.0), 1.5M NaCl for 5 minutes; and 6×SSC (1 M NaCl, 1 M Sodium Citrate) for 5 minutes. The filters were air-dried and then placed in a vacuum oven at 80° C. for 60 minutes. The filters were probed with a 1400 base pair BamHI-BglI fragment (biotin-labelled), as described above, from the AluI methylase gene. The DNA from the colonies producing a signal were purified and analyzed by restriction digests.

The clones with DNA that were resistant to AluI digestion were tested for the presence of any restriction activity. Twenty-five milliliter cultures of these positive clones (grown in Circle-Grow plus tetracycline) were used to prepare an extract for assaying restriction enzyme activity. A clone was identified which expresses the AluI methylase, but no AluI activity. It was possible that AluI activity was present in the host cells, but that the level of expression in *E. coli* was very low.

EXAMPLE 5

Analysis of AluI Methylase Clones

The AluI methylase positive clones were mapped with various restriction enzymes in order to subclone the gene coding for the AluI restriction enzyme in a higher copy plasmid. The results indicated the presence of a 6 kb BamHI fragment to the left of the methylase gene, and an 8 kb BamHI fragment to the right of the methylase gene. Since the genes coding for a methylase and a restriction enzyme are typically contiguous, one of the two BamHI fragments should contain the gene coding for the restriction enzyme. Therefore, both BamHI DNA fragments were subcloned separately in pUC19, and introduced into a host expressing AluI methylase which had been cloned in pACYC184 (pACYCAluIM1). Surprisingly, none of the clones displayed any detectable AluI restriction enzyme activity. Since one of these two subclones should contain the gene for the AluI restriction enzyme, it was possible that even in higher copy pUC19 the expression level is too low to be detected. Therefore, a new strategy was developed to determine the presence of a very low level of restriction enzyme activity in a crude extract of clones.

*E. coli* cell crude extract contains a variety of nucleases. A standard practice in cloning restriction-modification enzymes is to assay the activity in the crude extract. However, the presence of these non-specific nuclease activities interferes with the true restriction enzyme activity in the crude extract, particularly when the level of restriction enzyme expression is very low. Deoxyadenosine monophosphate (dAMP) and transfer RNA (tRNA) inhibit the activity of non-specific nucleases. Thus, AluI restriction endonuclease activity of the subclones was measured in the presence of dAMP and tRNA, as described below.

The restriction enzyme assay was performed by centrifuging a 20 to 25 ml overnight culture, and resuspending the cell pellets in 0.9 ml of cold SB (10 mM Tris, pH 7.5, 10 mM $\beta$-mercaptoethanol, 1 mM EDTA). The cells were transferred to a 1.5 ml microcentrifuge tube and sonicated three times with 10 second bursts at a 100 duty cycle using a microtip probe. The cellular debris was removed by centrifuging for 5 minutes at 12×g at 4° C. Lambda DNA substrate was prepared in 1 X REact 1 buffer (LTI) containing dAMP (1 mM) and tRNA (5 $\mu$g/ml). Five $\mu$l of the cell extract was serially diluted 3-fold through 3 more tubes. The reactions were incubated 30–60 minutes at 37° C., and analyzed on an agarose gel. A very low level of activity was determined by the presence of the appropriate size bands associated with an AluI digest of lambda DNA.

The results of the restriction enzyme assay suggest that one of the subclones confining the 6 kb BamHI fragment (pBJS76) displayed a very low level of AluI activity. Thus, subcloning in a high copy plasmid alone is not sufficient to produce cells that express detectable levels of AluI enzyme activity. The addition of dAMP and tRNA in the assay system is essential to isolate or identify clones that express AluI restriction enzyme.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference in their entirety.

What is claimed is:

1. A recombinant host cell comprising an Arthrobacter gene coding for a restriction endonuclease, said restriction endonuclease is capable of recognizing the palindromic sequence:

5' AG ↓ CT 3'
3' TC ↑ GA 5' and cleaving said sequence between the deoxyguanidine and deoxycytidine residues.

2. The host cell of claim 1, wherein said gene is obtained from *Arthrobacter luteus*.

3. The host cell of claim 2, wherein said gene is obtained from *Arthrobacter luteus* ATCC 21606.

4. The host cell of claim 1, wherein said gene codes for AluI.

5. A host cell of claim 1, wherein said host cell is *E. coli*.

6. A vector comprising an Arthrobacter gene coding for a restriction endonuclease, said restriction endonuclease is capable of recognizing the palindromic sequence:

5' AG ↓ CT 3'
3' TC ↑ GA 5' and cleaving said sequence between the deoxyguanidine and deoxycytidine residues.

7. The vector of claim 6, wherein said Arthrobacter gene codes for AluI.

8. The vector of claim 6, wherein said endonuclease gene is under control of an AluI endonuclease gene promoter.

9. The vector of claim 6, wherein said endonuclease gene is under control of an inducible promoter.

10. The vector of claim 9, wherein said promoter is lambda $P_L$ promoter.

11. The vector of claim 9, wherein said promoter is a tac promoter.

12. A method of producing a restriction endonuclease which recognizes the palindromic sequence:

5' AG ↓ CT 3'
3' TC ↑ GA 5' and cleaves said sequence between the deoxyguanidine and deoxycytidine residues, said method comprising:
 (a) culturing a recombinant host cell comprising an Arthrobacter gene coding for said restriction endonuclease; and
 (b) isolating said restriction endonuclease from said host cell.

13. The method of claim 12, wherein said gene is obtained from *Arthrobacter luteus*.

14. The method of claim 13, wherein said gene is obtained from *Arthrobacter luteus* ATCC 21606.

15. The method of claim 12, wherein said gene codes for AluI.

16. The method of claim 12, wherein said host cell is *E. coli*.

17. The method of claim 12, wherein said gene is contained in a vector.

18. The method of claim 12, wherein said endonuclease gene is under control of an AluI endonuclease gene promoter.

19. The method of claim 12, wherein said gene is under control of an inducible promoter.

20. The method of claim 19, wherein said promoter is a lambda $P_L$ promoter.

21. The method of claim 19, wherein said promoter is a tac promoter.

22. A method of using the vector of claim 6, to prepare a restriction endonuclease, said method comprising:
 (a) introducing said vector into a host cell to produce a recombinant host cell;
 (b) culturing said recombinant host cell; and
 (c) isolating said restriction endonuclease from said recombinant host cell.

* * * * *